United States Patent
Perkins

(10) Patent No.: US 8,040,238 B2
(45) Date of Patent: *Oct. 18, 2011

(54) WIRELESS TRACKING SYSTEM AND METHOD FOR BACKHAUL OF INFORMATION

(75) Inventor: Matthew R. Perkins, San Diego, CA (US)

(73) Assignee: Awarepoint Corporation, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/982,832

(22) Filed: Dec. 30, 2010

(65) Prior Publication Data

US 2011/0084809 A1    Apr. 14, 2011

Related U.S. Application Data

(63) Continuation of application No. 12/899,913, filed on Oct. 7, 2010.

(60) Provisional application No. 61/249,629, filed on Oct. 8, 2009.

(51) Int. Cl.
G08B 1/08 (2006.01)
G08B 13/14 (2006.01)
H04Q 5/22 (2006.01)

(52) U.S. Cl. ......... 340/539.13; 340/539.12; 340/539.11; 340/10.1; 340/572.1

(58) Field of Classification Search ............... 340/539.1, 340/539.11, 539.12, 539.13, 573.1, 10.1, 340/572.1
See application file for complete search history.

(56) References Cited

U.S. PATENT DOCUMENTS

| | | | |
|---|---|---|---|
| 5,812,865 A * | 9/1998 | Theimer et al. | 709/228 |
| 7,164,667 B2 | 1/2007 | Rayment et al. | |
| 7,336,182 B1 * | 2/2008 | Baranowski et al. | 340/572.1 |
| 7,366,120 B2 | 4/2008 | Handforth et al. | |
| 7,453,858 B2 | 11/2008 | Csapo et al. | |
| 7,466,985 B1 | 12/2008 | Handforth et al. | |
| 7,573,382 B2 * | 8/2009 | Choubey et al. | 340/539.13 |
| 7,580,729 B2 | 8/2009 | Ozluturk | |
| 7,660,559 B2 | 2/2010 | Herscovich et al. | |
| 7,688,762 B2 | 3/2010 | Douglas et al. | |
| 2008/0012767 A1 * | 1/2008 | Caliri et al. | 342/463 |
| 2009/0067333 A1 | 3/2009 | Ergen et al. | |
| 2009/0069642 A1 * | 3/2009 | Gao et al. | 600/300 |
| 2009/0213730 A1 | 8/2009 | Zeng et al. | |

* cited by examiner

*Primary Examiner* — Benjamin C Lee
*Assistant Examiner* — Omeed Alizada
(74) *Attorney, Agent, or Firm* — Clause Eight IPS; Michael Catania

(57) ABSTRACT

The present invention provides a solution to backhauling health information. The present invention utilizes a mesh network to backhaul the health information. The system includes a plurality of first tags, a mesh network, and an information engine. Each of the tags represents a first object. The mesh network preferably includes a plurality of plug-in sensors located within the facility. At least one node in the mesh network operates as healthcare device. The information engine is in communication with the mesh network and determines a position location of the healthcare device and an operation of the healthcare device.

3 Claims, 8 Drawing Sheets

WIRELESS TRACKING SYSTEM AND METHOD FOR BACKHAUL OF INFORMATION

CROSS REFERENCES TO RELATED APPLICATIONS

The present application is a continuation application of U.S. patent application Ser. No. 12/899,913, filed on Oct. 7, 2010, which claims priority to U.S. Provisional Patent Application No. 61/249,629, filed Oct. 8, 2009, now abandoned, both of which are hereby incorporated by reference in their entireties.

STATEMENT REGARDING FEDERALLY SPONSORED RESEARCH OR DEVELOPMENT

Not Applicable

BACKGROUND OF THE INVENTION

1. Field of the Invention

The present invention is related to wireless tracking systems and methods. More specifically, the present invention relates to a system and method for backhauling information over a mesh network.

2. Description of the Related Art

Real-time knowledge of resources, whether the resources are assets or people, is becoming a necessary tool of many businesses. Real-time knowledge of the location, status and movement of crucial resources can allow a business to operate more efficiently and with fewer errors. However, many businesses employ hundreds if not thousands of resources in a single facility, and these resources need to be accounted for by a central system that is user friendly.

For example, in a typical hospital there are numerous shifts of employees that utilize the same equipment. When a new shift arrives, the ability to quickly locate medical equipment not only results in a more efficient use of resources, but also can result in averting a medical emergency. Thus, the tracking of medical equipment in a hospital is becoming a standard practice.

The tracking of objects in other facilities is rapidly becoming a means of achieving greater efficiency. A typical radio frequency identification system includes at least multiple tagged objects, each of which transmits a signal, multiple receivers for receiving the transmissions from the tagged objects, and a processing means for analyzing the transmissions to determine the locations of the tagged objects within a predetermined environment.

Several prior art references discloses various tracking systems.

McKee et al., U.S. Pat. No. 6,915,135 discloses a system for determining presence, identity and duration of presence in a given area (a table in a restaurant) of an object (tag attached to a waiter).

Lester, U.S. Pat. No. 3,805,265 discloses a location system that uses line-of-sight radiant wave energy for signal transmission.

Schwengler U.S. Pat. No. 7,050,819, is directed at the problem of adequate power for a mobile telephone for a two-way communication function or a regeneration function as a node of a mesh network.

Christ, U.S. Pat. No. 5,977,913, discloses a radiofrequency system that is utilized within a prison and allows for an individual to be located after an alarm is triggered by the individual.

Zodnik, U.S. Patent Publication No. 2004/0147232, discloses wall-mounted (RJ-11 or RJ-45) wireless transceivers configured to only track the location of a self-identified wireless communication device in order to communicate the location of the self-identified wireless communication device to an emergency service such as 911.

Welch et al., U.S. Pat. No. 7,382,247 for a Personal Status Physiologic Monitor System And Architecture And Related Monitoring Methods, discloses a systems for monitoring a patient that uses a personal status monitoring device, such as a ECG electrode assembly, which transmits a signal to an intermediary device, such as a PDA, which transmits to a server using a WLAN.

Tessier et al., U.S. Pat. No. 7,403,111 for a Location System Using A First Signal To Gate A Second Signal, discloses an object identifier that transmits both an IR signal and a RF signal for location determination.

Dempsey et al., U.S. Pat. No. 7,053,831 for a Location System, discloses a system which allows for a location to be determined without requiring precise calculations through use of an object identifier that transmits one identifier corresponding to an object identifier and a second identifier which is a group identifier.

Dempsey, U.S. Pat. No. 7,099,895 for a System And Method For Performing Object Association Using A Location Tracking System, discloses a system for recording object associations based on signals for object identifiers.

Eagle et al., U.S. Patent Publication No. 2005/0250552, for a Combined Short Range Radio Network And Cellular Telephone Network For Interpersonal Communications, discloses a system that uses BLUETOOTH technology integrated in a cellular telephone to provide interpersonal communications between individuals.

As stated above, the problem is inadequate resource visibility in a business. Businesses such as hospitals, need to locate resources (assets and people), know the status of the resources, and understand the usage history of the resources to enable business improvement.

Specific problems for hospitals include tracking infections in a hospital to determine a source and other areas or individuals that may be infected. Other problems include spotting emerging patterns of infection and outbreaks to mitigate those affected. Further, for MEDICARE and other insurance providers, hospitals and other medical facilities need to demonstrate that patients received their required care in order to receive payment for such care. The prior art has failed to provide an adequate solution to these problems.

BRIEF SUMMARY OF THE INVENTION

The present invention provides a solution to transmitting health information. The present invention utilizes a mesh network that acts to backhaul information obtained utilizing a healthcare device.

One aspect of the present invention is a system for backhauling health information over a mesh network. The system includes a plurality of first tags, a mesh network, and an information engine. Each of the plurality of first tags represents a first object. The mesh network preferably includes a plurality of plug-in sensors located within the facility. At least one node in the mesh network operates as healthcare device. The information engine is in communication with the mesh network and determines a position location of the healthcare device and an operation of the healthcare device.

The first object is fixed or mobile. The healthcare device is preferably at least one of a fluid pump, heart monitor, ventilation pump and electrocardiogram. The mesh network preferably routes information from the healthcare device to a predetermined destination. The mesh network preferably transmits data related to who accessed the healthcare device last. The mesh network preferably transmits data related to how much time is left before the device needs to be serviced. The mesh network preferably transmits data related to what type of chemicals are in the healthcare device. The mesh network preferably transmits data related to the status of the device. The mesh network preferably provides firmware upgrades to the healthcare device. The healthcare device preferably operates as a RTLS device using one of ultrasound, infrared and radiofrequency medium.

Another aspect of the present invention is an enhanced-accuracy enterprise-wide real-time location system. The system includes a plurality of first tags and a mesh network. Each of the plurality of first tags represents a first object. The mesh network includes a plurality of sensors located within the facility. A plurality of nodes in the mesh network operate as RTLS devices using one of ultrasound, infrared, and a radiofrequency medium, wherein each of the plurality of end points transmit to at least one of a plurality of sensors in the mesh network. The mesh network routes RTLS information from each of the plurality of nodes to a predetermined destination.

The mesh network preferably operates as an RTLS and a backhaul for information from each of the plurality of end points. The mesh network preferably operates as a secondary RTLS system and a backhaul for information from each of the plurality of end points. Each of the plurality of end points preferably operates as a healthcare device. The healthcare device is preferably at least one of a fluid pump, heart monitor, ventilation pump and electrocardiogram. The mesh network preferably routes information from the healthcare device to a predetermined destination. The mesh network preferably transmits data related to who accessed the healthcare device last. The mesh network preferably transmits data related to how much time is left before the device needs to be serviced. The mesh network preferably transmits data related to what type of chemicals are in the healthcare device. The mesh network preferably transmits data related to the status of the device. The mesh network preferably provides firmware upgrades to the healthcare device. The healthcare device preferably operates as a RTLS device using one of ultrasound, infrared and radiofrequency medium.

A medium range wireless communication format is preferably selected from ZIGBEE communication format, Bluetooth communication format, Low-Power BlueTooth communication format, WiFi communication format, Low-Power WiFi communication format, Ultra Wide Band communication format, Ultrasound communication format or Infrared communication format.

Real time location systems, frequency abbreviated as RTLS, provide inherent characteristics which have both immediate tactical short-term benefits as well as long-term strategic implications for hospital operations. Real time location systems provide hospital administrators with actionable information regarding the location, status and movement of equipment and people. With RTLS, hospitals have access not only to the specific locations of equipment and people—but also advanced RTLS search capabilities allowing searching by specific location (floor, area, room) or unique asset identifier (department owner, type, manufacturer, model number, asset control number or EIN).

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

Figure 1:
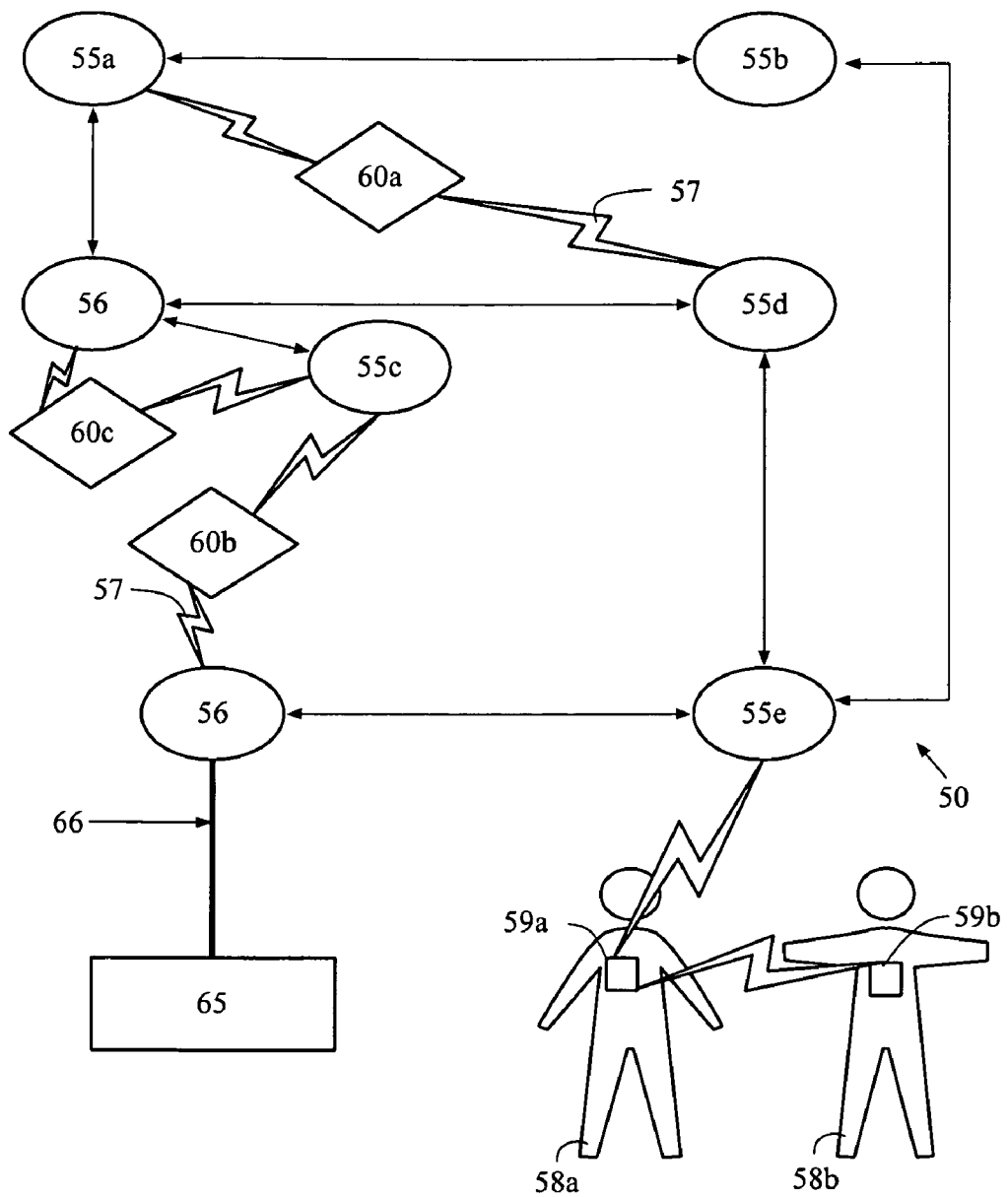
FIG. 1 is schematic view of a system for analyzing an interaction between objects.
Figure 2:
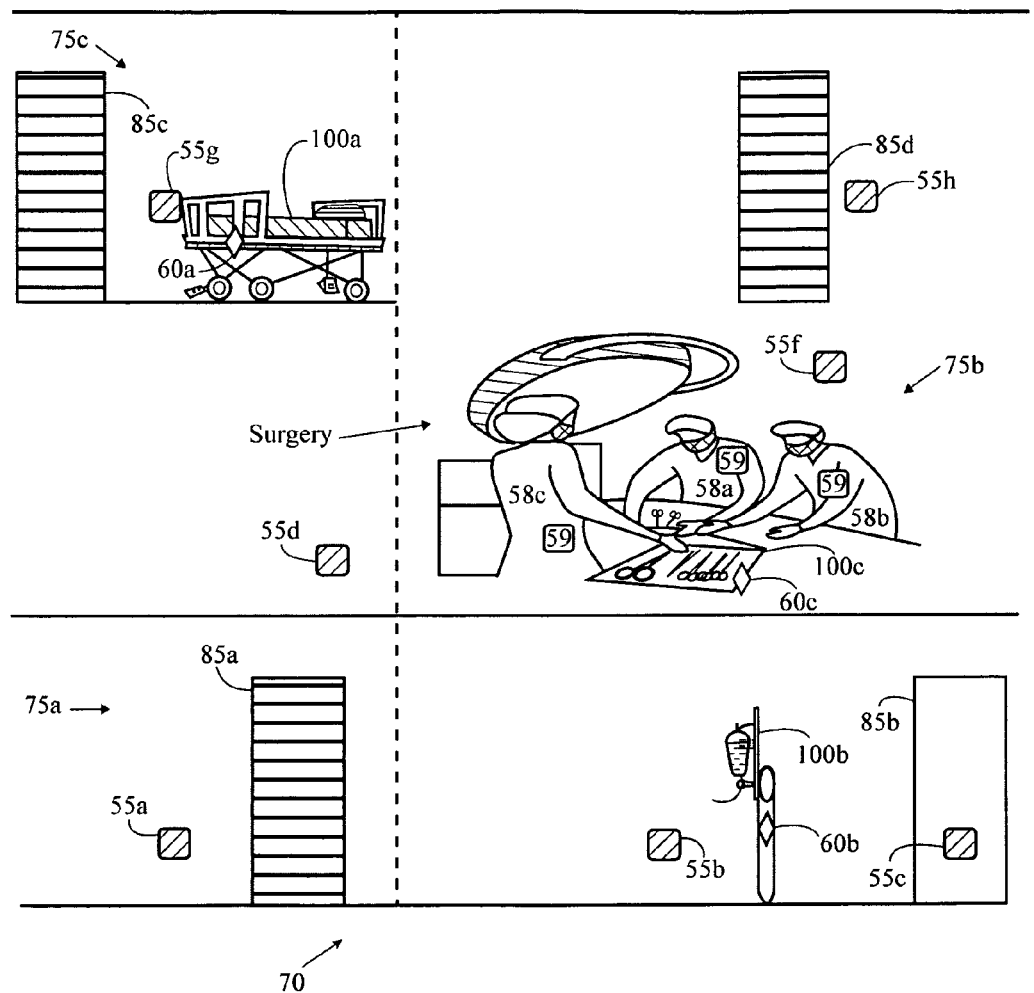
FIG. 2 is a multi-floor view of a facility employing a system for analyzing an interaction between objects.
Figure 3:
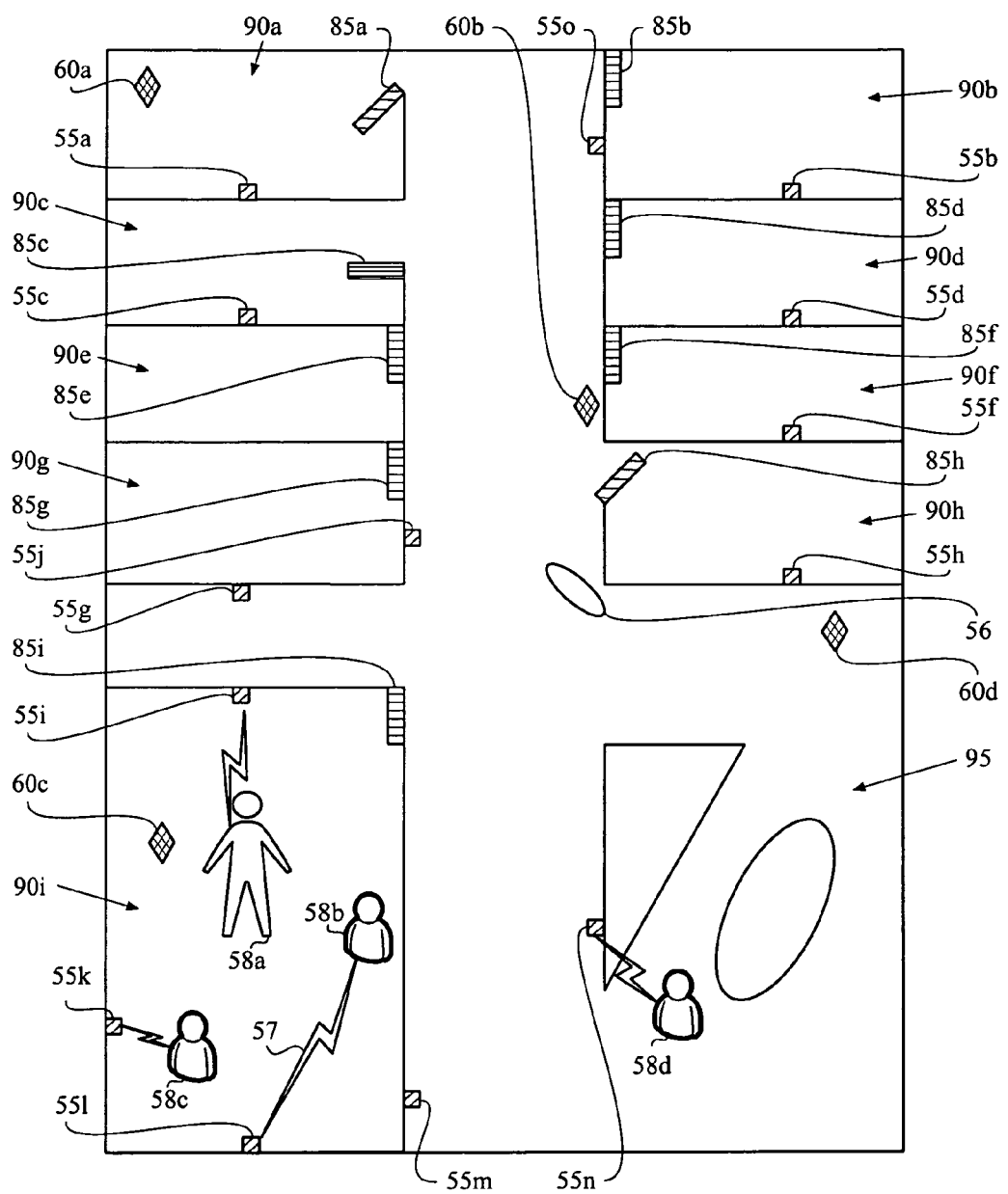
FIG. 3 is a floor plan view of a single floor in a facility employing the system for analyzing an interaction between objects.

As shown in FIGS. 1-3, a system for tracking objects within a facility is generally designated 50. The system 50 is capable of analyzing an interaction between objects, individuals 58 and/or devices 100. and the system backhauls information over a mesh network to an information engine 65 for processing. The system 50 preferably includes a plurality of sensors 55, a plurality of bridges 56, a plurality of communication devices 59, a plurality of tags 60, and at least one information engine 65. The sensors 55 form a mesh network for receiving signals from the communication devices 59 and tags 60. One example of the components of the system 50 is disclosed in U.S. Pat. No. 7,197,326, for a Wireless Position Location And Tracking System, which is hereby incorporated by reference in its entirety. A more specific example of the sensors 55 is disclosed in U.S. Pat. No. 7,324,824, for a Plug-In Network Appliance, which is hereby incorporated by reference in its entirety. Another wireless tracking system and method is Perkins et al., U.S. patent application Ser. No. 12/885,509, filed on Sep. 18, 2010, for a Wireless Tracking System And Method Utilizing Near Field Communication Devices, which is hereby incorporated by reference in its entirety. Yet another wireless tracking system and method is Perkins et al., U.S. patent application Ser. No. 12/484,236, filed on Jun. 14, 2009, for a Wireless Tracking System And Method For Analyzing An Interaction Between Objects, which is hereby incorporated by reference in its entirety.

The system 50 is preferably employed at a facility 70 such as a business office, factory, home, hospital and/or government agency building. The system 50 is preferably utilized to backhaul information over the mesh network from various objects positioned throughout the facility 70 in order to analyze real time information pertaining to the object at an information engine 65. The system 50 also tracks the location of objects in the facility 70. The communication devices 59 and tags 60 preferably continuously transmit signals on a predetermined time cycle, and these signals are received by sensors 55 positioned throughout the facility 70. Alternatively, the tags 60 and communication devices 59 transmit signals in a random, ad-hoc or dynamic manner, and these signals are received by the sensors 55 positioned throughout the facility 70. The sensors 55 transmit the data from the communication devices 59 and tags 60 to a bridge 56 for transmission to the information engine 65. If a sensor 55 is unable to transmit to a bridge 56, the sensor 55 may transmit to another sensor 55 in a mesh network for eventual transmission to a bridge 56. In a preferred embodiment, a transmission may be sent from a transmission distance of six sensors 55 from a bridge 56. Alternatively, a transmission is sent from a transmission distance ranging from ten to twenty sensors 55 from a bridge 56. The information engine 65 preferably continuously receives transmissions from the mesh network formed by the sensors 55 via the bridges 56 concerning the operation of objects 100 bearing the communication device 59 and/or bearing a tag 60 within the facility 70. The information engine 65 processes the transmissions from the sensors 55 and calculates a real-time position for each of the objects and data concerning the object 100 within the facility 70. The real-time location information for each of the objects is preferably displayed on a graphical user interface ("GUI"). A floor plan image may also be used with a graphical user interface of a computer, personal digital assistant, or the like so that an individual of the facility 70 is able to quickly locate objects 100 within the facility 70, know the real-time status of the object (is the object in operation, in need of maintenance, or similar information).

As shown in FIG. 1, the system 50 utilizes sensors 55 to monitor and identify the real-time status and position of objects 100 bearing or integrated with communication devices 59. The sensors 55a-f preferably wirelessly communicate with each other (shown as double arrow lines) and with an information engine 65 through a wired connection 66 via at least one bridge 56, such as disclosed in the above-mentioned U.S. Pat. No. 7,324,824 for a Plug-In Network Appliance. The communication devices 59 and tags 60 transmit wireless signals 57 which are received by the sensors 55a-e, which then transmit signals to bridges 56 for eventual transmission to the information engine 65. The information engine 65 is preferably located on-site at the facility 70. However, the system 50 may also include an off-site information engine 65, not shown.

In a preferred embodiment, each communication device 59 and tag 60 preferably transmits a radio frequency signal of approximately 2.48 GigaHertz ("GHz"). The communication format is preferably IEEE Standard 802.15.4. Alternatively, each communication device 59 and tag 60 transmits an infrared signal or an ultrasound signal. Each device preferably contains a low-power, medium-range (1 foot to 30 feet) wireless communication system. Such wireless communication systems include ZIGBEE, BLUETOOTH, Low-Power BLUETOOTH, WiFi or Low-Power WiFi, Ultra Wide Band ("UWB"), Ultrasound and Infrared communication systems. The wireless communication system is used to exchange device specific information after the low-power short-range system has indicated that an interaction has occurred. Those skilled in the pertinent art will recognize that the wireless communication system can also be used independent of the low-power short-range system for other wireless communication applications such as location and tracking, sense and control, building automation, smart energy, telecom applications, consumer building automation, remote control applications, home health care, personal fitness, personal wellness, and many other applications. The tags 60 may be constructed with an asset theft protection system such as disclosed in Baranowski et al., U.S. Pat. No. 7,443,297 for a Wireless Tracking System And Method With Optical Tag Removal Detection, which is hereby incorporated by reference in its entirety. The tags 60 and communication devices 59 may be designed to avoid multipath errors such as disclosed in Nierenberg et al., U.S. Pat. No. 7,504,928 for a Wireless Tracking System And Method Utilizing Tags With Variable Power Level Transmissions, and Caliri et al., U.S. Patent Publication No. 2008/0012767 for a Wireless Tracking System And Method With Multipath Error Mitigation, both of which are hereby incorporated by reference in their entireties.

As shown in FIGS. 2-3, the facility 70 is depicted as a hospital. The facility 70 has multiple floors 75a-c. Each floor 75a, 75b and 75c has multiple rooms 90a-i, with each room 90 accessible through a door 85. Positioned throughout the facility 70 are sensors 55a-o for obtaining readings from communication devices 59 and tags 60 attached to people or devices. A bridge 56 is also shown for receiving transmissions from the sensors 55 for backhauling the information over the mesh network to the information engine 65. For example, as shown in FIG. 2, the system 50 determines that individuals 58a, 58b and 58c are located in a surgery room and are using device 100c, which is a surgical kit. The information engine 65 analyzes the interaction by monitoring the duration of the interaction, the devices 100 utilized, the location of the interaction (surgery), the previous location of the individuals 58 (possibly a surgical prep room) and additional factors. Also shown in FIG. 2, information pertaining to a fluid pump 100b is sent from the fluid pump 100b, acting as a node in the mesh network, to the sensor 55 for backhauling over the mesh network to the information engine 65. The backhauled information provides a current, real time status of the fluid pump, what types of chemicals are contained within it, the levels of the chemicals, the temperature, and other valuable information. Thus, a hospital can obtain valuable information about its equipment, machines, and the like, without having to use a human resource to obtain the information since the information is backhauled over the mesh network to at least one information engine 65 for analysis and display on a GUI if required.

In another example, as shown in FIG. 3, the system 50 determines that individuals 58a, 58b and 58c are located in a patient's room and are using device with an attached tag 60c, which is a patient monitoring device. In this example, individual 58a is a patient, individual 58b is a physician, and individual 58c is a nurse. The information engine 65 analyzes the interaction by monitoring the duration of the interaction, the devices 100 utilized, the location of the interaction (patient's room), the previous location of the individuals 58 and additional factors. The information engine 65 uses this data to generate billing information for the patient.

Figure 4:
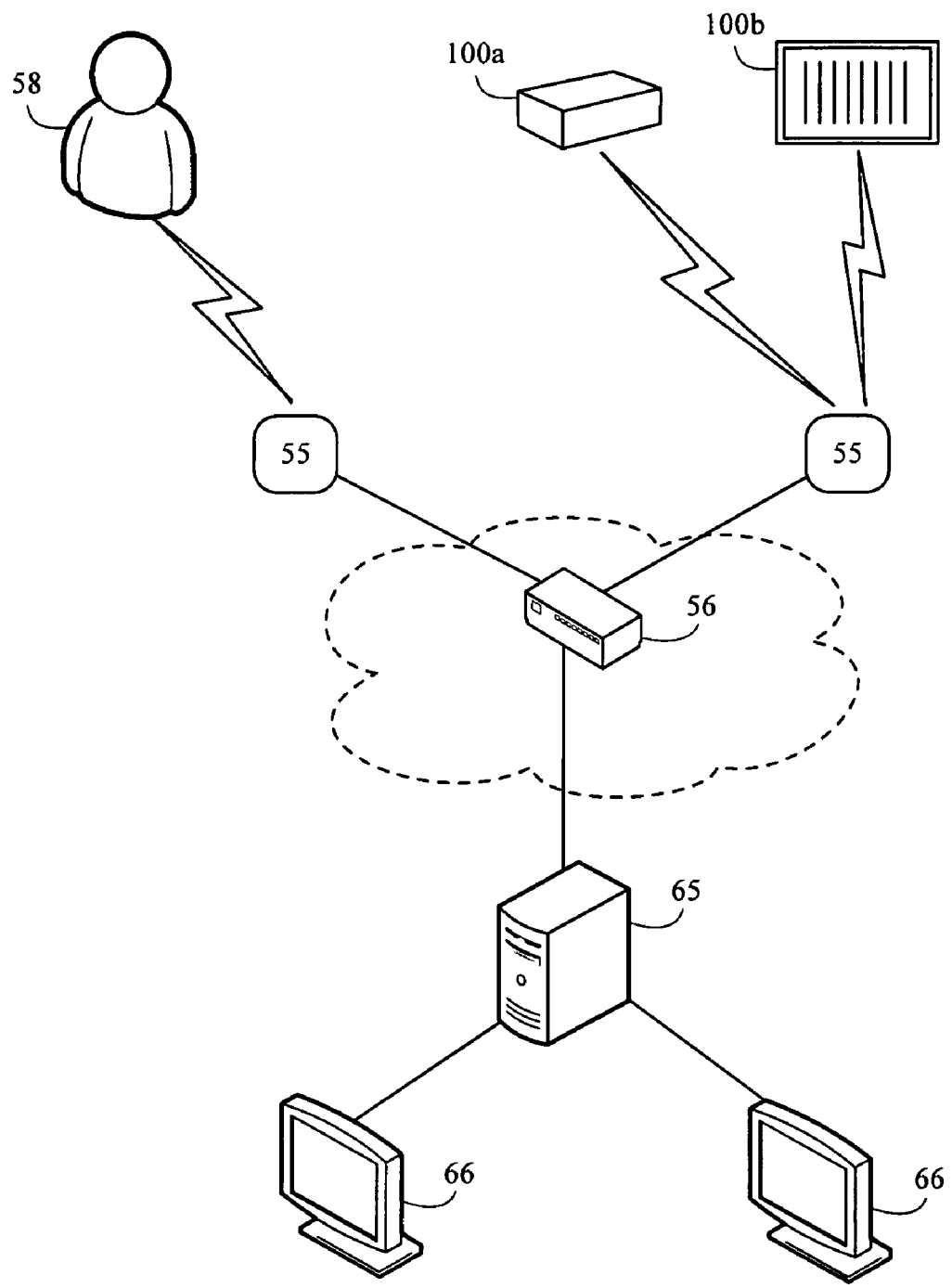
FIG. 4 is a block diagram of a flow of information utilizing a system for analyzing an interaction between objects.

FIG. 4 illustrates a preferred architecture of the system 50. For description purposes, the information providers are set forth on one side of the network and the operations is set forth on the other side of the network. However, those skilled in the pertinent art will recognize that the illustrated architecture of the system 50 is not meant to limit any physical relationship between information providers and operations. In fact, an individual 58 could be tracked while accessing information from a device 100 such as a computer 66 in operations. The information providers include individuals 58 that wear communication devices 59, an electrocardiogram having a communication device 60, sterilizable equipment 100b bearing sterilizable tags 60, and the like. A description of sterilizable tags 60 is found in Caliri et al., U.S. patent application Ser. No. 12/325,030 for Wireless Tracking System And Method With Extreme Temperature Resistant Tag, which is hereby incorporated by reference in its entirety. A bridge 56 acts as an intermediary between the backhaul information and the information engine. The bridge 56 communicates information to the information engine 65 which analyzes the information to determine an interaction between objects for access through an enterprise local area network for display on computers 66 or other graphical user interface devices.

Figure 5:
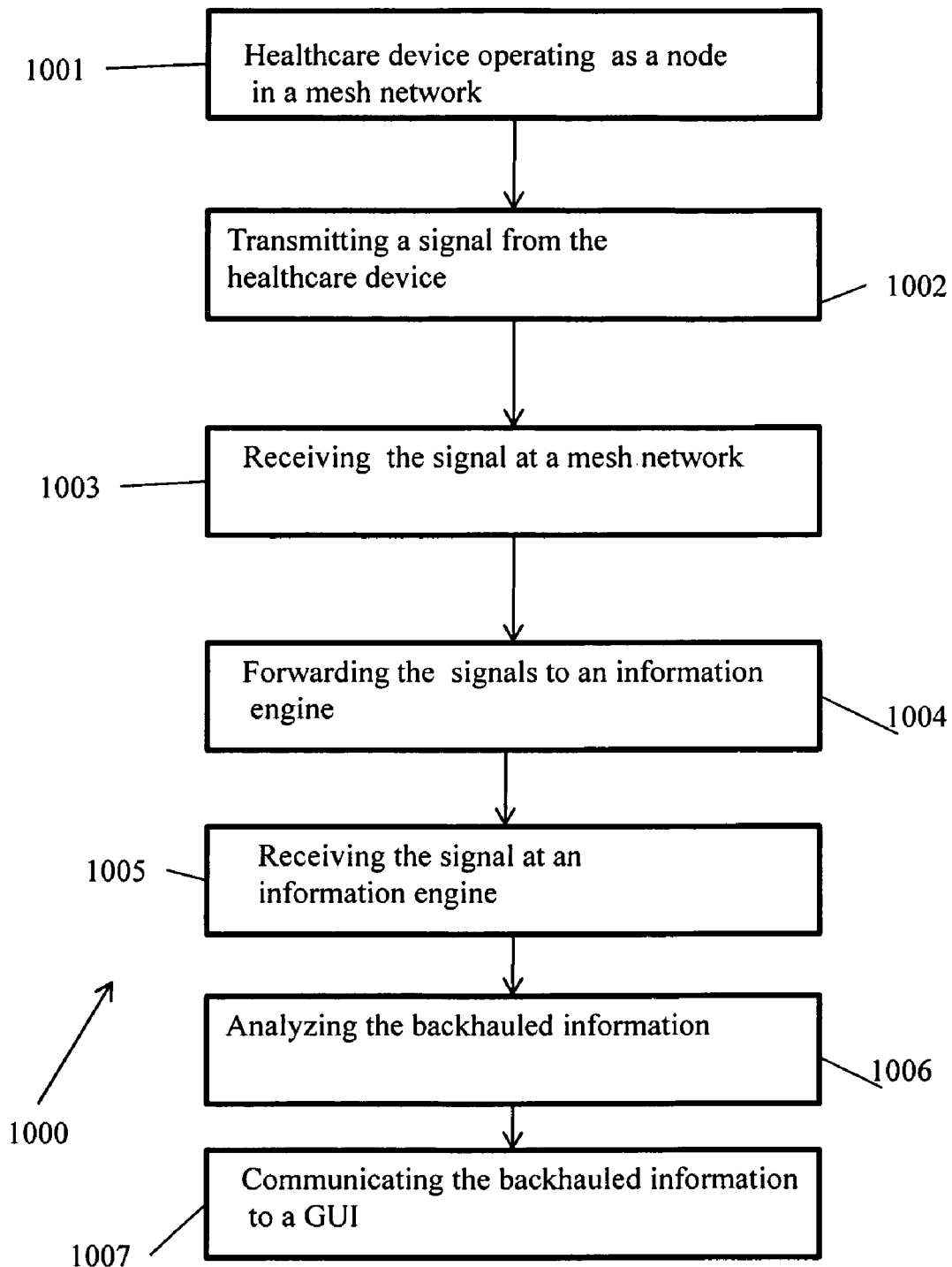
FIG. 5 is a flow chart of a method for analyzing an interaction between objects.

A method 1000 for backhauling information over a mesh network is illustrated in FIG. 5. At block 1001, a communication device associated with an object, in this case a ventilation pump, operates as a node in the mesh network and a healthcare device. The ventilation pump also operates as a RTLS device. At block 1002, a wireless signal is transmitted from the ventilation pump using a medium power communication protocol such as ultrasound, infrared and radiofrequency. At block 1003, the first wireless signal is received at at least one of a plurality of sensors positioned within a facility. At block 1004, the signal is forwarded over the mesh network using a communication protocol such as ZIGBEE. At block 1005, the signal is received at an information engine. At block 1006, the information engine analyzes the backhauled information on the signal for a multiple of factors. The multiple factors include a status of the device, a position location of an action, a duration of the action, a previous location of the device prior to the action, and information for other objects or persons within a predetermined distance of the location of the action. At block 1007, the backhauled information is communicated to a graphical user interface.

Figure 6:
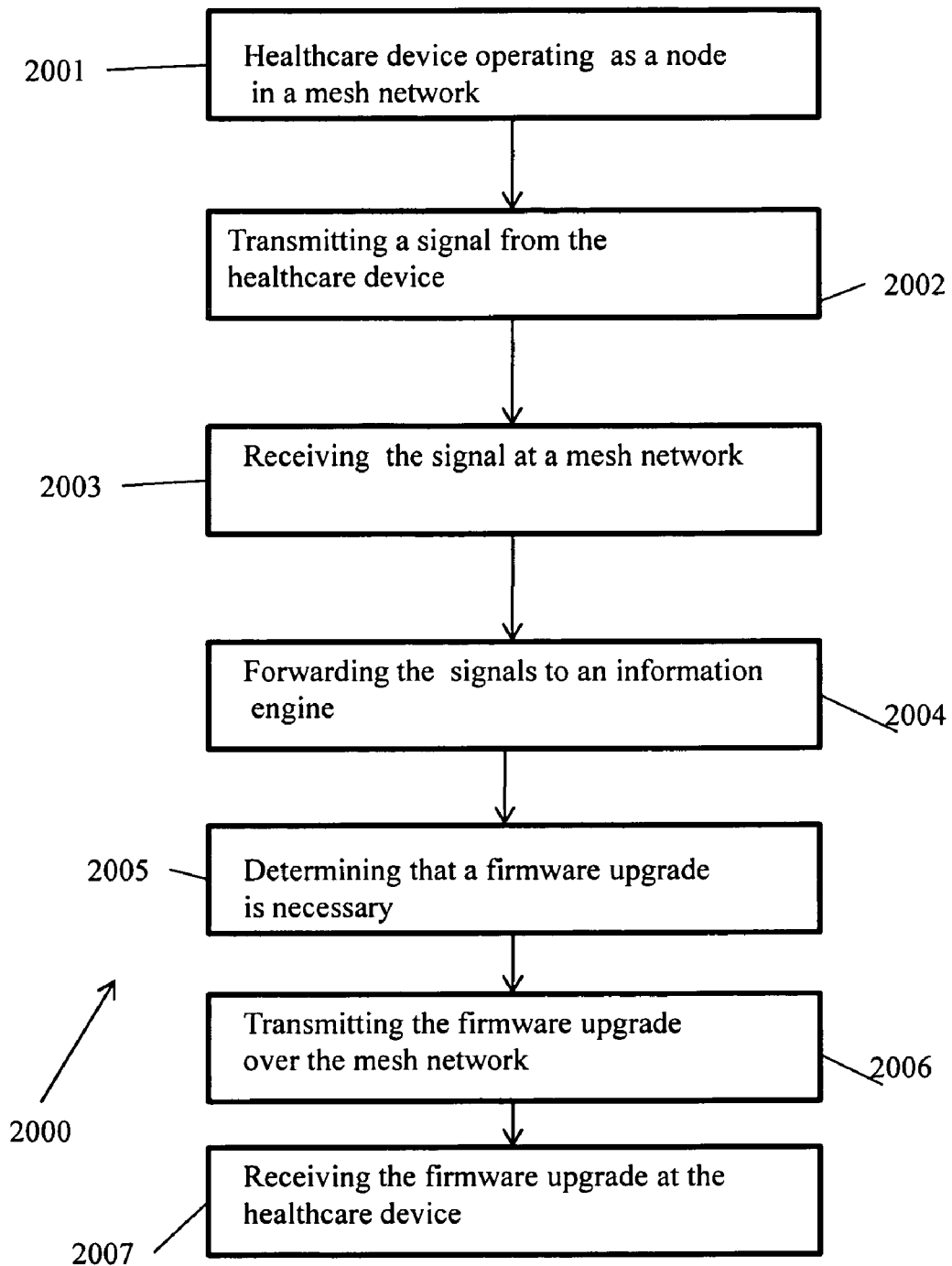
FIG. 6 is a flow chart of a method for analyzing an interaction between objects.

Another method 2000 for backhauling information over a mesh network is illustrated in FIG. 6. At block 2001, a healthcare device operates as a RTLS device and as a node in a mesh network. In this example, the healthcare device is a heart rate monitor. At block 2002, a wireless signal is transmitted from the healthcare device using a medium power communication protocol such as ultrasound, infrared and radiofrequency. At block 2003, the first wireless signal is received at at least one of a plurality of sensors positioned within a facility. At block 2004, the signal is forwarded to an information engine. At block 2005, the information engine determines that a firmware upgrade is needed at the healthcare device. At block 2006, the information engine through the mesh network transmits the firmware upgrade to the healthcare device. At block 2007, the healthcare device receives the firmware and performs an upgrade of its firmware.

Figure 7:
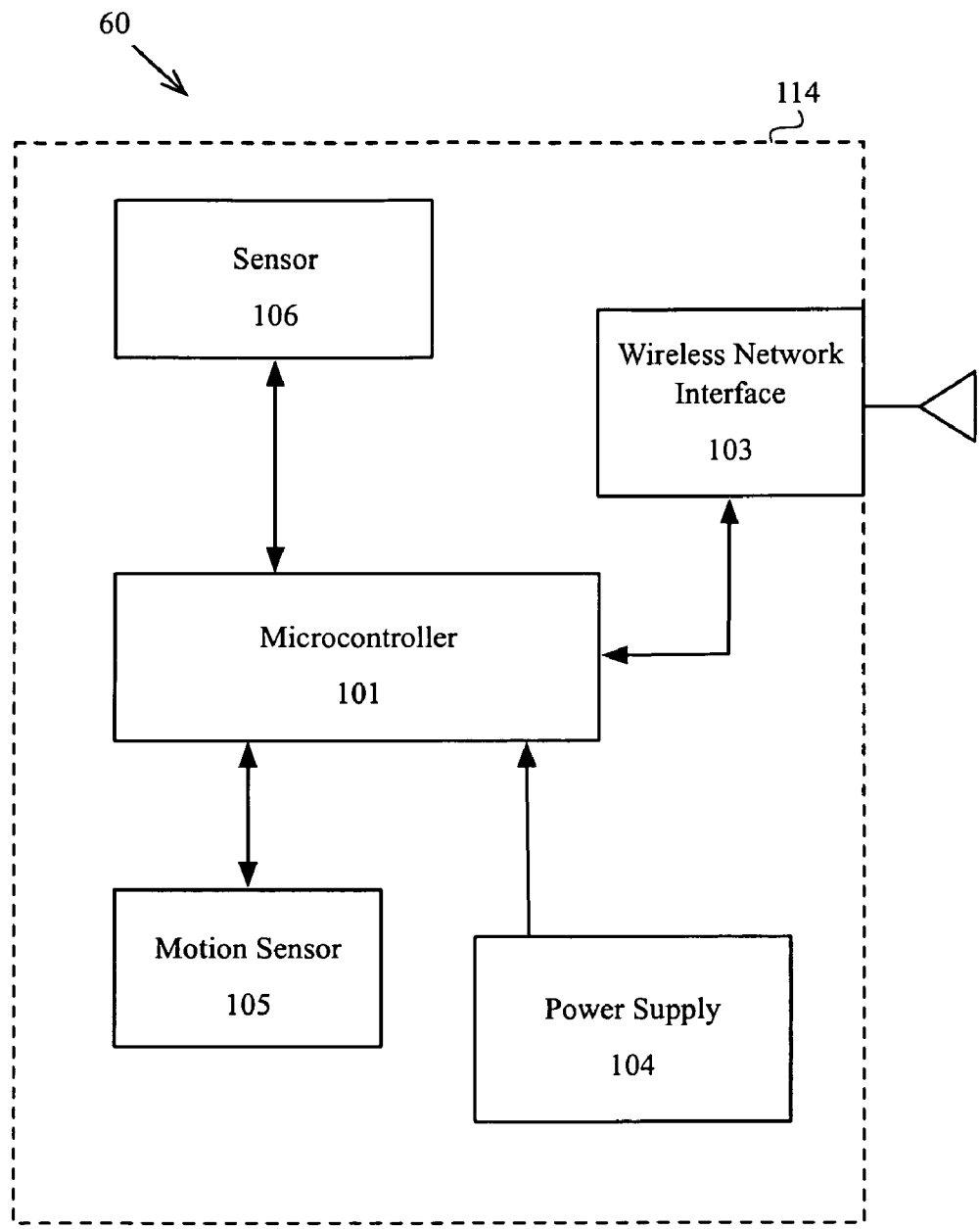
FIG. 7 is a block diagram of a tag.

A tag 60 utilized with a device 100 is illustrated in FIG. 7. The tag 60 preferably includes a microcontroller 101, a transceiver 103, a power supply 104 and a sensor 106. Alternatively, the tag 60 includes a motion sensor 105. The transmissions are transmitted through transceiver 103. A power supply 104 provides power to the tag 60. All of the components are preferably contained within a housing 107. A communication device 59 preferably has the same components and structure of the tag 60 illustrated in FIG. 7.

Figure 8:
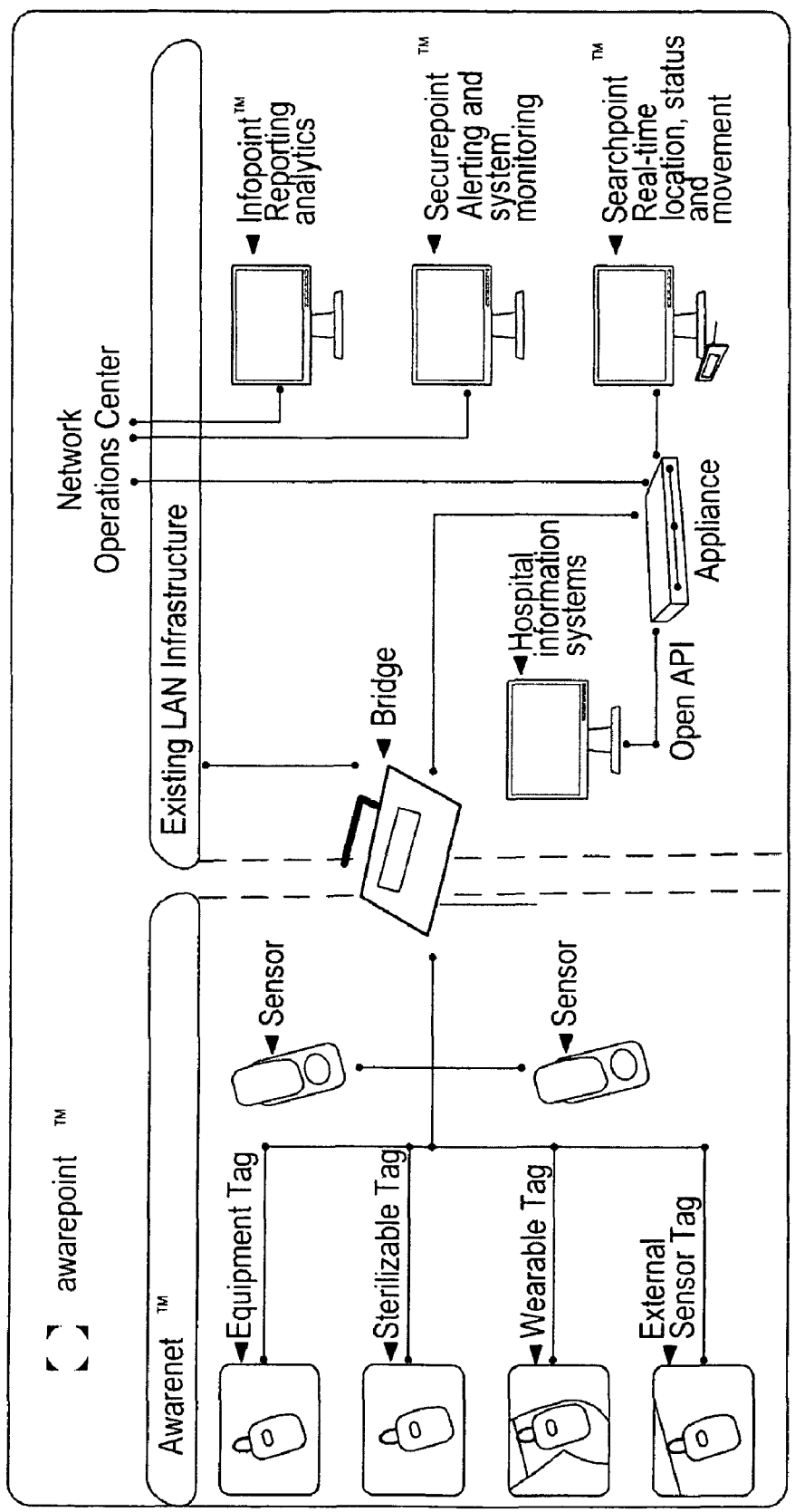
FIG. 8 is a plan view of an identification badge containing a communication device.

FIG. 8 is a block diagram of a system for determining a real-time location of an object. Sensors receive the messages from the broadcasting tags through attached different antennas, calculate the signal strength, and decide which signal strength to use. The signal strength information is routed to the server for location processing. Bridge/appliance/server devices received signal strength information from the high definitions sensors and make location decisions. The tag sends broadcast messages preferably using ZIGBEE based wireless transmissions. The sensors receive the ZIGBEE based wireless transmissions preferably through two spatially and angularly diverse antennas. Software on each sensor preferably identifies and matches the sending tag and received signal strength readings. Software on each sensor preferably makes local decisions on the final signal strength value for the transponder. Each sensor preferably sends the signal strength information to the appliance through a wireless ZIGBEE based wireless transmission network. The tags and sensors communicate to the bridges preferably through a ZIGBEE based wireless transmission network. The location of the tags is preferably calculated by using the paired signal strength between tags and the sensors that hear the tag. Time slicing is also utilized in determining a real-time location of the object within an indoor facility by making time slots available in each antenna.

A patient wears, or has attached, a patient tag 60a and a plurality of medical devices bearing or integrated with tags 60b. Such healthcare devices may include blood pressure monitors, dialysis devices, respiration aids, oxygen tanks, wheelchairs, and the like, and all may act as nodes in a mesh network. The plurality of network monitors preferably utilize ZIGBEE networking standards and technology, such as disclosed at zigbee.org, which pertinent parts are hereby incorporated by reference.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

I claim as my invention:

1. An Enhanced-Accuracy Enterprise-Wide Real-Time Locating System (RTLS), the system comprising:
   a plurality of tags, each of the plurality of tags representing a mobile object, each of the plurality of tags transmitting a periodic signal using a first wireless communication format;
   a mesh network comprising a plurality of sensors located within a facility, each sensor of the plurality of sensors communicating with other sensors of the plurality of sensors utilizing the first wireless communication format; and
   a plurality of end points in the mesh network that operate as healthcare devices using a second wireless communication format selected from one of ultrasound, infrared, and a radiofrequency medium, wherein each of the plurality of end points transmit only to at least one of a plurality of sensors in the mesh network utilizing the second wireless communication format to backhaul information over the mesh network;
   wherein the mesh network routes RTLS information from each of the plurality of end points and each of the plurality of tags to an information engine for processing to track each mobile object represented by each of the plurality of tags and to collect data on each of the healthcare devices from the backhaul information transmitted over the mesh network, the data comprising at least one of a status of a healthcare device, a healthcare device service date, a chemical in the healthcare device, a temperature of the healthcare device, a chemical level of the healthcare device, a motion signature of a healthcare device, and a last person that accessed a healthcare device;
   wherein each of the plurality of end points in the mesh network that operate as a healthcare device has a priority of operating as a healthcare device and the backhauling of information over the second wireless communication format allows for real-time communication from the healthcare device to the information engine.

2. The system according to claim 1 wherein the healthcare devices are at least one of a fluid pump, heart monitor, ventilation pump, weight scale, blood pressure monitor, glucose monitor and electrocardiogram.

3. The system according to claim 1 wherein the mesh network routes healthcare information from at least one of the healthcare devices.

* * * * *